United States Patent
Allard

(10) Patent No.: US 10,525,251 B2
(45) Date of Patent: Jan. 7, 2020

(54) MEDICAL STOPCOCK, KIT COMPRISING SUCH A STOPCOCK, AND METHOD FOR PREPARING A MIXTURE OR AN EMULSION

(71) Applicant: Guerbet, Villepinte (FR)

(72) Inventor: Ludovic Allard, Millery (FR)

(73) Assignee: Guerbet, Villepinte (FR)

( * ) Notice: Subject to any disclaimer, the term of this patent is extended or adjusted under 35 U.S.C. 154(b) by 113 days.

(21) Appl. No.: 15/565,764

(22) PCT Filed: Apr. 15, 2016

(86) PCT No.: PCT/EP2016/058453
§ 371 (c)(1),
(2) Date: Oct. 11, 2017

(87) PCT Pub. No.: WO2016/166346
PCT Pub. Date: Oct. 20, 2016

(65) Prior Publication Data
US 2018/0117297 A1 May 3, 2018

(30) Foreign Application Priority Data
Apr. 15, 2015 (FR) ...................................... 15 53325

(51) Int. Cl.
*A61M 39/22* (2006.01)
*A61M 39/10* (2006.01)
*A61J 1/20* (2006.01)

(52) U.S. Cl.
CPC ........ *A61M 39/223* (2013.01); *A61M 39/105* (2013.01); *A61J 1/2058* (2015.05);
(Continued)

(58) Field of Classification Search
CPC .... A61M 39/10; A61M 5/284; A61M 5/3134; A61M 5/31513; A61M 5/3129;
(Continued)

(56) References Cited

U.S. PATENT DOCUMENTS 2,703,586 A     3/1955   Asker
3,157,201 A * 11/1964   Littmann ............ A61M 39/223
                                                                             137/625.47
(Continued)

FOREIGN PATENT DOCUMENTS

CN          1662762 A     8/2005
CN       101516434 A     8/2009
(Continued)

OTHER PUBLICATIONS

Idée et al., "Use of Lipiodol as a Drug-Delivery System for Transcatheter Arterial chemoembolization of Hepatocellular Carcinoma: A Review", Oncology/Hematology, 2013, pp. 530-549, vol. 88, No. 3.

(Continued)

*Primary Examiner* — Manuel A Mendez
(74) *Attorney, Agent, or Firm* — Thompson Coburn LLP; Steven M. Ritchey

(57) ABSTRACT

A medical stopcock comprising a body provided with at least two female connectors and a male connector; a mobile plug which is mounted in the body, is provided with a rotation lever and comprises a fluid circulation channel; and a reinforcement collar rigidly connected to at least two of the connectors; wherein the reinforcement collar is spaced apart from the body in order to form an openworked zone around the central body.

15 Claims, 5 Drawing Sheets

(52) U.S. Cl.
CPC ............... *A61M 2039/1033* (2013.01); *A61M 2039/1083* (2013.01); *A61M 2039/1094* (2013.01); *A61M 2039/229* (2013.01); *A61M 2205/276* (2013.01); *A61M 2205/583* (2013.01)

(58) Field of Classification Search
CPC .... A61M 39/26; A61M 39/045; A61M 39/22; A61M 5/007; A61M 5/28; A61M 5/14546; A61M 5/2448; A61J 1/20; A61J 1/2093; A61B 17/00491; A61B 17/8822
See application file for complete search history.

(56) References Cited

U.S. PATENT DOCUMENTS

| | | | | |
|---|---|---|---|---|
| 3,161,195 | A * | 12/1964 | Taylor | A61M 5/284 137/853 |
| 4,217,933 | A | 8/1980 | Perry, Jr. et al. | |
| 4,471,765 | A * | 9/1984 | Strauss | A61M 5/007 600/432 |
| 4,807,666 | A * | 2/1989 | Morse | F16K 5/0492 137/625.47 |
| 5,868,250 | A * | 2/1999 | Brackett | A61M 5/008 206/363 |
| 6,349,850 | B1 | 2/2002 | Cheikh | |
| 7,306,768 | B2 * | 12/2007 | Chiga | A61M 5/165 210/232 |
| 7,785,312 | B2 * | 8/2010 | Thorne, Jr. | A61J 1/2096 604/500 |
| 8,308,340 | B2 * | 11/2012 | Ferrante | A61B 17/00491 222/137 |
| 9,061,129 | B2 | 6/2015 | Lauer | |
| 9,212,762 | B2 | 12/2015 | Duncan | |
| 2003/0181850 | A1 * | 9/2003 | Diamond | A61M 39/223 604/30 |
| 2008/0121297 | A1 * | 5/2008 | Indigne | F16K 41/103 137/625.47 |
| 2013/0030348 | A1 | 1/2013 | Lauer | |
| 2014/0008366 | A1 * | 1/2014 | Genosar | A61M 5/1782 220/265 |
| 2014/0276215 | A1 | 9/2014 | Nelson et al. | |

FOREIGN PATENT DOCUMENTS

| | | |
|---|---|---|
| CN | 102575783 A | 11/2012 |
| CN | 103889500 A | 6/2014 |
| EP | 1504207 B1 | 4/2009 |
| EP | 2078536 A1 | 7/2009 |
| FR | 2804609 A1 | 8/2001 |
| RU | 2201743 C2 | 4/2003 |
| WO | 03093704 A1 | 11/2003 |
| WO | 2008/009946 A1 | 1/2008 |
| WO | 2008/057946 A2 | 5/2008 |
| WO | 2012/024370 A1 | 2/2012 |
| WO | 2014/090958 A1 | 6/2014 |

OTHER PUBLICATIONS

International search report for PCT/EP2016/058453 dated Sep. 27, 2016.
Nakamura et al., "Transcatheter Oily Chemoembolization of Hepatocellular Carcinoma", Radiology, 1989, pp. 783-786, vol. 170.
Written opinion for PCT/EP2016/058453 dated Sep. 27, 2016.
Office action received in Russian Application No. 2017136138 dated Aug. 8, 2019.
Office action received in Chinese Application No. 201680021379.1 with English translation, dated Oct. 22, 2019, 13 pages.

* cited by examiner

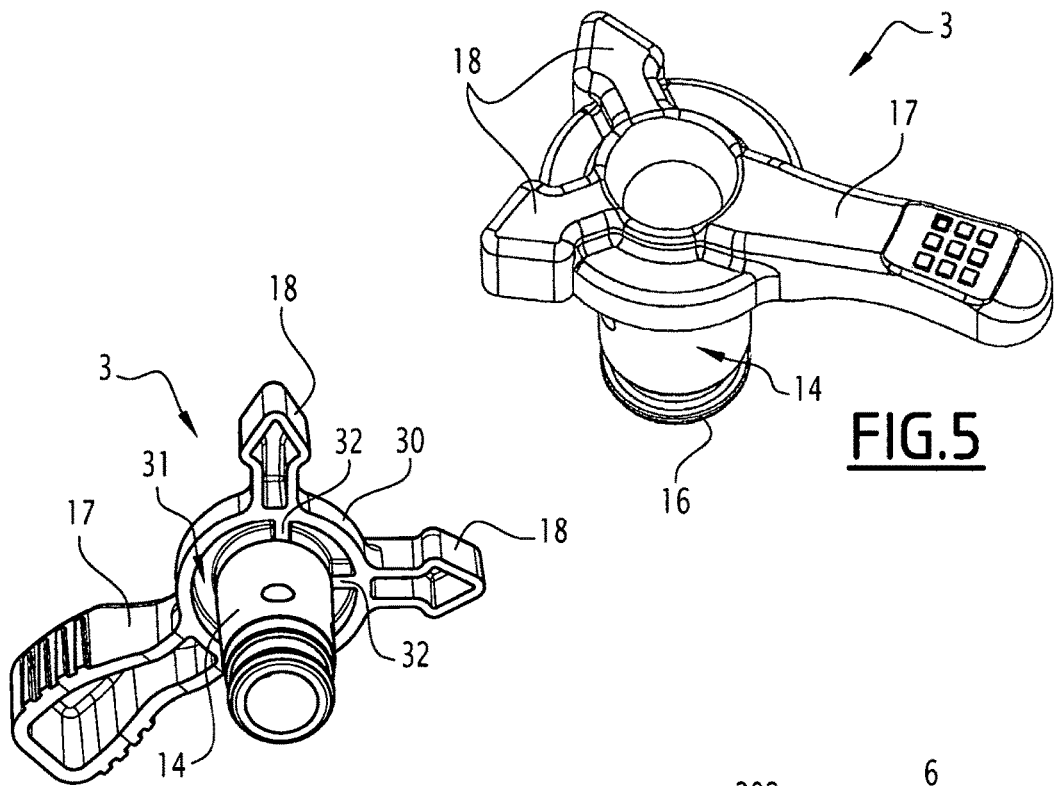
FIG.5
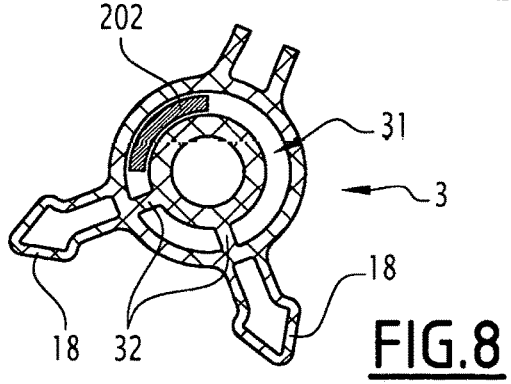
FIG.6
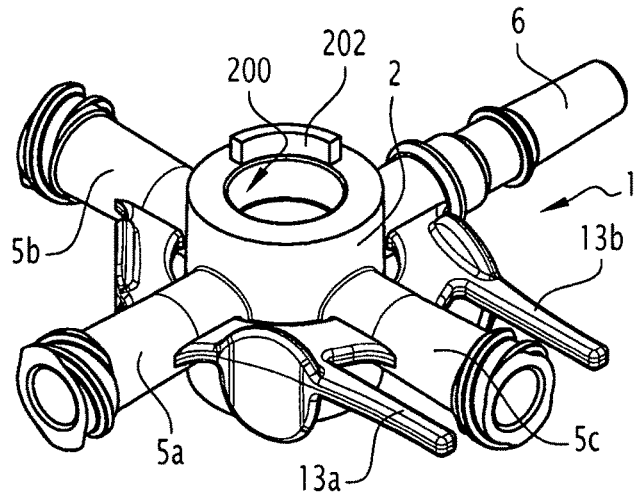
FIG.7
FIG.8

MEDICAL STOPCOCK, KIT COMPRISING SUCH A STOPCOCK, AND METHOD FOR PREPARING A MIXTURE OR AN EMULSION

CROSS-REFERENCE TO RELATED APPLICATIONS

This application is a U.S. National Phase application of PCT/EP2016/058453, filed on Apr. 15, 2016, claiming the benefit of French Application No. 1553325, filed on Apr. 15, 2015, both of which are incorporated herein by reference in their entireties.

The invention relates to a medical stopcock, to a kit for preparing a product to be injected, preferably a mixture or an emulsion, said kit comprising such a medical stopcock, and to a method for preparing a mixture or an emulsion intended to be injected into a patient, said method being carried out with the aid of such a preparation kit.

The iodinated oil Lipiodol® has been used now for almost thirty years in interventional radiology. This product is characterized by its propensity to be captured selectively by hepatic tumors. This iodinated oil is therefore used as an anticancer agent vector for the treatment of hepatocellular carcinoma in a technique referred to as TransArterial ChemoEmbolization (c-TACE) (Nakamura et al.: Radiology, 1989; 170:783-6 and J. M. Idée-B. Guiu: Critical Reviews in Oncology/Hematology, 2013; 88(3):530-49). The iodinated oils, in particular Lipiodol®, are also known to induce a transient embolization of the arterial circulation, thereby causing the latter to slow down. Given that most anticancer agents are soluble in water, the "emulsion" form, which is designed for mixing two phases that are non-soluble in each other, appears to be the most judicious for mixing an iodinated oil and an anticancer agent. It appears to be the most suitable for transporting, and delivering to a tumor, an anticancer agent that is too toxic and not sufficiently effective when administered in non-emulsified form by an intra-arterial route or systemic route.

To perform c-TACE, an interventional radiologist prepares the emulsion extemporaneously, just before the injection. He traditionally uses two 50-ml syringes connected to a stopcock which has three ports and which is provided with two female connectors, to which the syringes are connected, and a male connector, to which a catheter or a microcatheter can be fixed. One of the syringes contains a solution of an anticancer agent, while the other syringe contains an iodinated oil such as Lipiodol®. The emulsion is obtained, for example, after ten successive and rapid passages of the content of one syringe to the other, with the aid of a three-way stopcock. The emulsion is then transferred into one of the two mixing syringes, the empty mixing syringe is disconnected from the stopcock, and an injection syringe is then put in the place of the mixing syringe that has been removed. A small quantity of emulsion is transferred into the injection syringe by actuating the piston of the remaining mixing syringe. The injection is performed, over the course of ten minutes, into the right or left branch of the hepatic artery of a patient, irrigating the major part of the tumor.

Given that several successive injections are sometimes performed, the emulsion remaining in the mixing syringe is sometimes mixed again in the manner described above, after disconnection of the injection syringe and reconnection of the second mixing syringe. A new injection is performed after the transfer of the emulsion into one of the two mixing syringes, the disconnection of the empty mixing syringe from the stopcock, the connection of an injection syringe in place of the mixing syringe that has been removed, and the transfer of a small quantity of emulsion into the injection syringe by actuating the piston of the remaining mixing syringe.

The stopcocks made of plastic that are currently on the market and are intended for medical use, in particular intended for preparation of an emulsion that will be injected into a patient in the context of a transarterial chemoembolization technique, are for the most part stopcocks with three ports, and they pose different problems for the interventional radiologist performing this technique.

Stopcocks made of plastic and intended for medical use, such as those known from FR 2 804 609, in most cases do not hold up when the manipulation of the devices connected to them generates excessive tension on the connection ports. These stopcocks break, and leaks thus appear at the base of these connection ports. This fragility may also be exacerbated by chemical attacks caused by certain products passing through these stopcocks.

These stopcocks made of plastic are manufactured by injection of a plastic in a mold. The strengthening of these stopcocks in order to improve their solidity has the disadvantage that, during their manufacture, there is an increased risk of shrink marks forming in their body. The shrink marks are defects of manufacturing, and more precisely of injection, which appear when the plastic part cools, under the effect of contraction of the plastic. They appear as a depression situated near the solid parts of the plastic part and on the plane surfaces. The position of the shrink marks does not vary from one injection to another, since it is linked to the design of the part and not to the injection parameters. These shrink marks increase the risk of leaks occurring in these devices.

WO 2008/057946 describes a medical stopcock composed of a body comprising an inlet port and two outlet ports, and of a plug which is inserted into the body and which, by rotation, permits communication between the inlet port and the outlet port of the stopcock. One of the technical problems that arises in the manufacture of this stopcock is that, during the step of steam sterilization, the heat has a tendency to deform and shrink the body of the stopcock, which is made from polyvinyl chloride (PVC). This problem can be solved by using a more rigid material such as polycarbonate or stainless steel. However, these materials may lead to other problems, for example insufficient leak-tightness of the ports to the entry and escape of the fluids. Nor does this document mention the problems associated with shrink marks.

High-pressure perfusion stopcocks are also known from the prior art, in particular from the patent EP 1 504 207. This patent describes a high-pressure stopcock composed of a stopcock body and of a plug that is provided with a fin. The body of the stopcock comprises an inlet port, at least one outlet port, and a collar rigidly connected to the inlet and outlet ports of the stopcock and of the central barrel of this stopcock, making it possible to stiffen the body of the stopcock in order to better resist the mechanical and chemical stresses to which the stopcock is subjected. However, such a stopcock still has the disadvantage of the formation of shrink marks inside the seat of the plug, or central barrel, during its manufacture, hence problems of potential leaks.

It is also known from the prior art, in particular from the U.S. Pat. No. 4,807,666, to reinforce the structure of a stopcock by the presence of a flange between the thicker edges of the collar and the barrel of the stopcock. Such a flange will have the effect of "aspirating" the plastic material from the hottest zone to the coldest zone during the cooling and shrinkage of the plastic material. This phenomenon, described extensively in the prior art, causes shrink marks to appear in the barrel of the stopcock body, which is generally a zone that is more difficult to cool than the exterior of the barrel.

It is these disadvantages that the invention is intended to overcome by making available a novel medical stopcock whose quality of manufacture is improved.

To this end, the invention relates to a medical stopcock comprising a body provided with at least two female connectors and a male connector, a mobile plug which is mounted in the body, is provided with a rotation lever and comprises a fluid circulation channel, and a reinforcement collar rigidly connected to at least two of the connectors, the reinforcement collar being spaced apart from the body in order to form an openworked zone around the central body.

By virtue of the invention, the mechanical stresses that arise during the use of the medical stopcock are concentrated at the intersections of the collar with the connectors, in a zone distanced from the central body of the stopcock.

Preferably, according to the invention, the body of the stopcock comprises:
- at least two female connectors and a male connector, preferably three female connectors and a male connector,
- a barrel in which the plug is inserted, and
- the reinforcement collar.

According to advantageous but non-obligatory aspects of the invention, such a stopcock can incorporate one or more of the following features, in any technically admissible combination:
- The stopcock comprises four connectors, of which three are female connectors, and the reinforcement collar is rigidly connected to three or four connectors.
- The medical stopcock comprises at least two gripping means designed for the placement of a finger, and the gripping means are situated on the reinforcement collar.
- At least one of the female connectors is designed to receive an injection syringe and comprises a foolproofing device in order to prevent a mixing syringe from being mounted on this connector, and this foolproofing device is formed by two projections which extend from the reinforcement collar and are provided on each side of the female connector designed to receive an injection syringe and form insertion spaces with respect to this connector.
- The projections make it possible to prevent the mounting of syringes that are provided with a means prohibiting their connection to the female connector designed to receive an injection syringe.
- The reinforcement collar is made of the same material as the body.
- The reinforcement collar is made of a material different than that of the body and that of the plug.
- The reinforcement collar is made of a fiber-reinforced material and is overmolded on the body.
- The plug is made of a material that is softer than the body and/or than the reinforcement collar.
- The reinforcement collar has a width greater than its thickness, preferably a width 3 to 10 times greater than its thickness.

It is considered that the invention also relates to a medical assembly comprising a stopcock as mentioned above, at least one mixing syringe, and at least one injection syringe.

The invention also relates to a preparation kit for preparing a product to be injected, preferably a mixture or an emulsion, said kit comprising a medical stopcock as mentioned above, two mixing syringes designed to be connected to a first and a second female connector of the stopcock, and an injection syringe designed to collect at least some of the product obtained by the mixing of the contents of the mixing syringes, effected by a reciprocating motion of the pistons of said mixing syringes, and designed to be connected to one of the female connectors of the stopcock.

According to advantageous but non-obligatory aspects of the invention, such a stopcock can incorporate one or more of the following features, in any technically admissible combination:
- One of the female connectors of the stopcock comprises a foolproofing device, and the mixing syringes comprise a means prohibiting their connection to said female connector.
- The mixing syringes comprise fins at their end.

The invention also relates to a method for preparing a mixture or an emulsion intended for injection into a patient, said method comprising steps of:
a) connecting two mixing syringes to two corresponding female connectors of a medical stopcock as mentioned above;
b) mixing an aqueous solution, contained in one of the mixing syringes, with an oil contained in the other mixing syringe after positioning a plug of the medical stopcock in such a way as to bring the mixing syringes into fluidic communication with each other, and effecting a reciprocating motion of the pistons of these mixing syringes until a mixture or an emulsion is obtained;
c) connecting an injection syringe to a specific connector of the medical stopcock or in place of the mixing syringes;
d) transferring some or all of the mixture or emulsion obtained in step b) into the injection syringe after positioning the plug in such a way as to bring one of the mixing syringes into communication with the injection syringe.

According to an advantageous but non-obligatory aspect of the invention, such a preparation method can additionally comprise a supplementary step consisting in connecting a downstream device, preferably a catheter or a microcatheter, to a male connector of the medical stopcock, this step being either concomitant with step a), or subsequent to step b), or concomitant with step c), or subsequent to step d).

The invention will be better understood, and other advantages thereof will become more clearly apparent, in light of the following description of a medical stopcock, of a kit for preparing a product to be injected, preferably a mixture or an emulsion, and of a method for preparing a product, preferably a mixture or an emulsion in accordance with its principle, said description being given by way of a non-limiting example and with reference to the attached drawings, in which:

FIG. 5 is a perspective view of the plug from FIG. 4, at a different angle;

FIG. 6 is a perspective view of another embodiment of a plug, at another angle;

FIG. 7 is a perspective view of the medical stopcock from FIG. 1, of which the plug is omitted;

FIG. 8 is a cross section of the medical stopcock from FIGS. 1 and 2, in a plane passing through the base of a lever of the plug;

Figure 1:
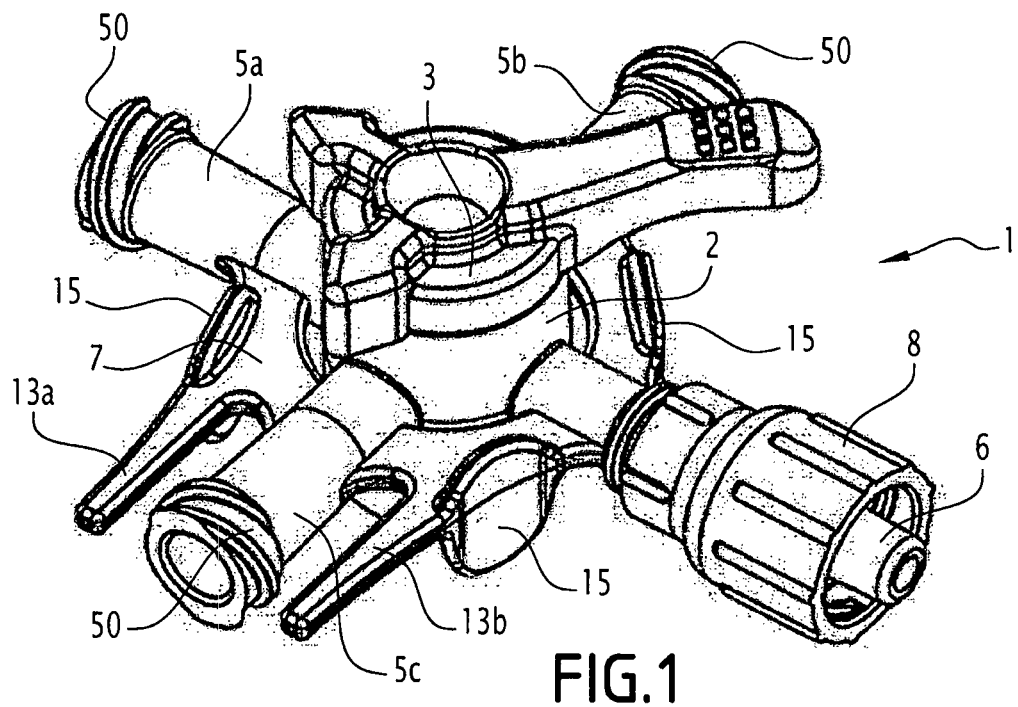
FIG. 1 is a perspective view of a medical stopcock according to the invention.
Figure 2:
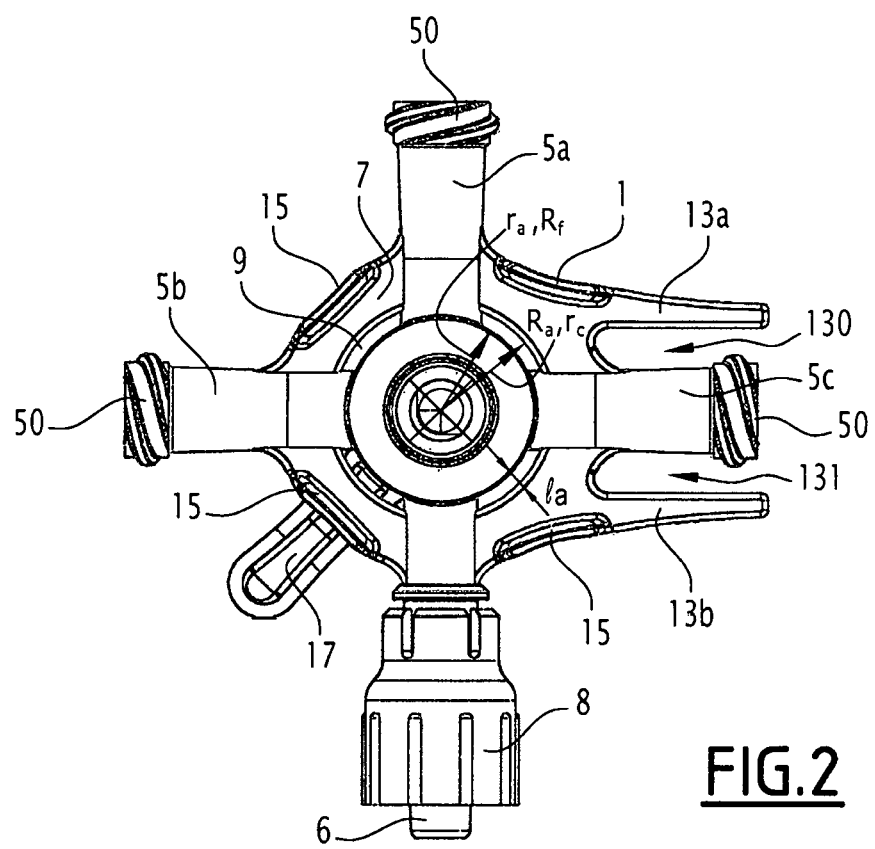
FIG. 2 is a plan view of the medical stopcock from FIG. 1.
Figure 3:
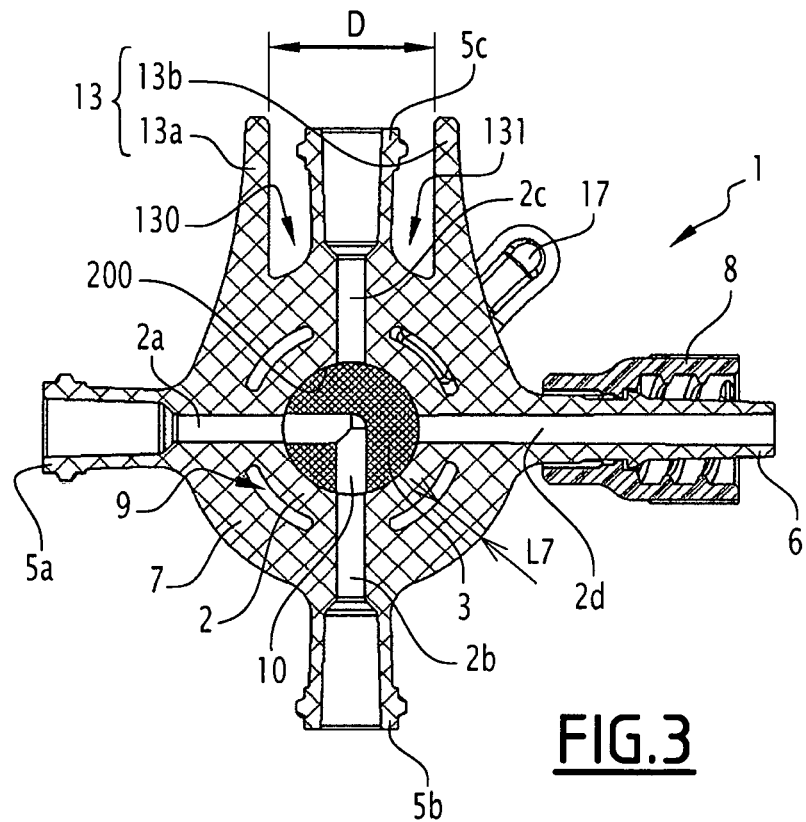
FIG. 3 is a cross section of the medical stopcock from FIGS. 1 and 2, in a plane comprising the central axes of four connectors of the medical stopcock.

FIGS. 1 to 3 show a medical stopcock 1 permitting the preparation of a mixture, preferably an emulsion, intended to be injected into a patient. The medical stopcock 1 comprises a hollow body 2 from which there extend three female connectors 5a, 5b and 5c and a male connector 6, preferably a Luer connector. The body 2 comprises a barrel of cylindrical shape delimiting a central bore 200, from which there extend four conduits 2a, 2b, 2c and 2d passing through the barrel and extending respectively through the connectors 5a, 5b, 5c and 6.

Figure 4:
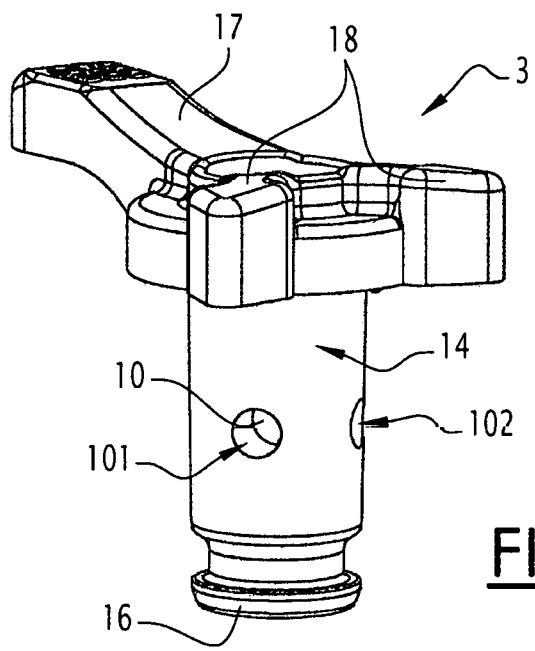
FIG. 4 is a perspective view of a plug of the medical stopcock from FIGS. 1 to 3.

The stopcock 1 comprises a plug 3, shown in particular in FIGS. 4 and 5, mounted rotatably in the bore 200. The plug 3 comprises a fluid circulation channel 10 for bringing the conduits 2a, 2b, 2c and 2d into communication in a manner described below. The plug 3 comprises an outer cylindrical wall 14 for ensuring the leaktightness of the stopcock 1 with the bore 200. An axial end of the plug 3 comprises a collar 16 with which it is held in the body 2 by clip fastening.

There are other solutions for holding the plug 3 in the body 2, for example snap riveting or the addition of a retention piece. Within the meaning of the present invention, "snap riveting" is understood as the creation of a mechanical bond between the plug 3 and the body 2, causing the partial deformation of the plug 3.

The plug 3 preferably comprises a lever 17 that can be actuated by a user, permitting the rotation of the plug 3 about its central axis.

According to an optional aspect of the invention, one of the female connectors, the connector 5c in the example shown, comprises a foolproofing device 13. A "foolproofing device" is understood to mean a mechanical device by which it is possible to avoid connection errors by providing a visual indication and by defining a mechanical configuration that prevents the use of undesired elements. In the example shown, the foolproofing device 13 comprises two projections 13a and 13b which are provided on each side of the female connector 5c and which define two insertion spaces 130 and 131 that are situated between the projections 13a and 13b, respectively, and the connector 5c.

The foolproofing device 13 preferably prevents the connection of a syringe whose volume is greater than a predetermined value, by virtue of the geometry of the projections 13a and 13b and the width of the spaces 130 and 131, or of a syringe provided with a means prohibiting its connection to the connector comprising this foolproofing device 13 and/or these projections 13a and 13b, on account of the incompatibility between this means and the mechanical configuration defined by the foolproofing device 13 and/or the projections 13a and 13b of this foolproofing device 13. Even more preferably, the foolproofing device 13 and advantageously the projections 13a and 13b of this foolproofing device 13 make it possible to prevent the mounting of syringes 20 and 21, preferably mixing syringes, provided with a means prohibiting their connection to the connector comprising this foolproofing device 13 and/or the projections 13a and 13b of this foolproofing device. Preferably, when the projections 13a and 13b prevent the connection of a syringe provided with a means prohibiting its connection to the female connector 5c comprising this foolproofing device 13 and/or these projections 13a and 13b, on account of the incompatibility between this means and the mechanical configuration defined by the foolproofing device and/or the projections of this foolproofing device, they do not protrude more than 5 mm beyond the end of the female connector 5c. Preferably, when the projections 13a and 13b prevent the connection of a syringe whose reservoir has a diameter greater than a threshold value corresponding to a maximum volume, preferably of a mixing syringe, they protrude more than 5 mm beyond the end of the female connector.

Figure 9:
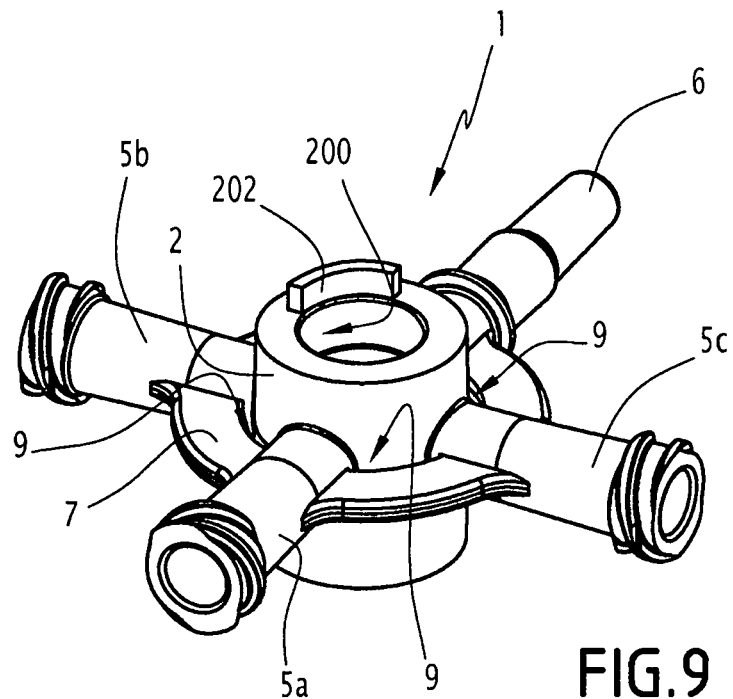
FIG. 9 is a perspective view of a medical stopcock according to a second embodiment of the invention.
Figure 10:
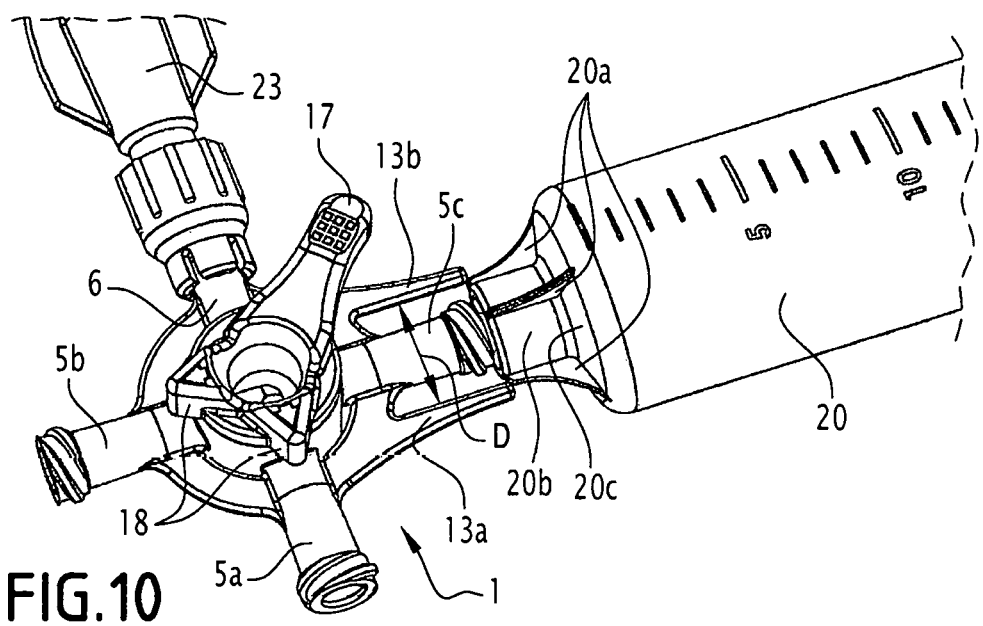
FIG. 10 is a perspective view of the medical stopcock from FIGS. 1 to 3, of a catheter connected to a connector of the medical stopcock, and a mixing syringe positioned in front of a female connector of the medical stopcock.
Figure 11:
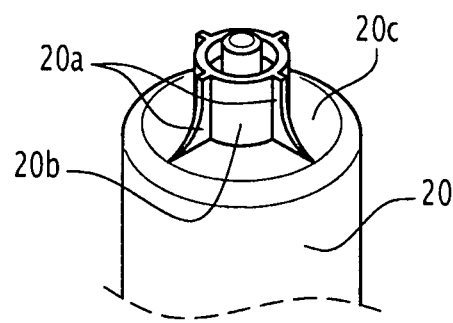
FIG. 11 is a perspective view of the end of a mixing syringe.

In the example shown in FIG. 10, the mixing syringe 20 is provided with means prohibiting its connection to the connector 5c comprising the foolproofing device 13. In this embodiment, the mixing syringe 20 comprises, at its end, fins 20a that form the means for prohibiting the connection of the mixing syringe 20 to the connector 5c comprising a foolproofing device. To screw a mixing syringe onto a female connector, preferably of the Luer type, it is necessary to effect between one and two turns of the syringe, depending on the connector. Thus, the mixing syringe 20 comprises at least one fin 20a, preferably at least two fins 20a. This allows the foolproofing device 13 to perform its function. The end of the mixing syringe 20 is formed by a Luer connector comprising an inner male thread provided on a peripheral skirt 20b. The fins 20a are provided on the outer surface of the skirt 20b. As is shown in FIG. 9, the fins 20a create an obstruction at the end of the mixing syringe 20, around the skirt 20b of the male thread of the Luer connector, which obstruction is of a size greater than the distance D between the projections 13a and 13b. More preferably, the mixing syringe 20 comprises, at its end, four fins 20a positioned at 90° with respect to each other. This permits a better dimensional equilibrium of the body of the syringe and also permits better ergonomics in terms of gripping the syringe. The fins 20a of the mixing syringe 20 preferably have a shape for generating an interference with the projections 13a and 13b of the foolproofing device 13. Advantageously, these fins 20a make it easier to screw the mixing syringe 20 onto the connectors 5a or 5b, by improving the gripping of the syringe. Advantageously, the fins are contiguous to the outer skirt 20b of the male Luer lock thread and also to a conical end zone 20c of the reservoir of the syringe. These fins 20a preferably have an outer shape in the form of an arc of a circle. This allows the fingers to be placed on these fins and ensures good gripping of the mixing syringe 20 while remaining atraumatic.

The mixing syringe 21 is also provided with such a geometry.

The connectors 5a, 5b and 5c comprise a thread 50, to which a connection means permitting leaktight assembly of a medical device is connected. This connection means is preferably a Luer connector, which is the standard means of connection in the medical field and which is screwed onto the thread 50. This connection means attaches to the reservoir of the syringe. The projections 13a and 13b allow the insertion spaces 130 and 131 to be dimensioned in such a way that it is impossible to introduce therein syringes having a reservoir with a diameter greater than a threshold value corresponding to a maximum volume, or in such a way that it is impossible to connect a syringe on account of the incompatibility between at least one means present on said syringe and the mechanical configuration defined by the projections 13a and 13b.

The foolproofing device 13 preferably prevents the mounting, on the connector 5c, of syringes that have a means prohibiting their connection to the mechanical configuration defined by the foolproofing device, or syringes whose volume is greater than 3 ml. More preferably, the foolproofing device 13 makes it possible to prevent the mounting, on the connector 5c, of syringes having at least one means for prohibiting their connection to the mechanical configuration defined by the foolproofing device. The presence of fins at the end of the mixing syringes 20 and 21 prohibits their connection to the mechanical configuration defined by the foolproofing device, as is shown in FIG. 9. Thus, in this embodiment, it is not possible to connect a mixing syringe to the female connector 5c.

Figure 12:
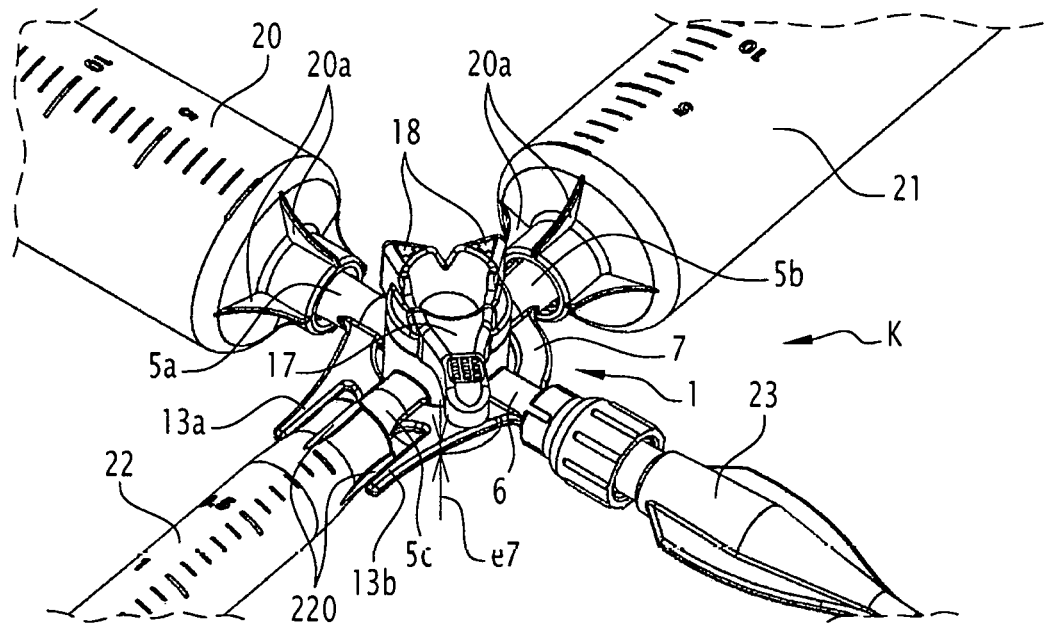
FIG. 12 is a perspective view of part of a preparation kit according to the invention.

The female connector 5c is preferably designed to be connected to an injection syringe 22, as is shown in FIG. 12. The external diameter of this syringe 22 and/or the size of the end of this syringe 22 allow it to be inserted into the insertion spaces 130 and 131 when it is screwed onto the connector 5c. At its distal end, the injection syringe 22 preferably comprises gripping beads 220 which have a size smaller than the distance D between the projections 13a and 13b.

In another embodiment, a syringe with a volume greater than 3 ml, like a mixing syringe 20, will not be able to be mounted on the connector 5c because its reservoir has too large a diameter.

The connectors 5a and 5b do not have a foolproofing device 13 and are therefore designed for the mounting of mixing syringes, as is shown in FIG. 12, in which two mixing syringes 20 and 21 are mounted on the connectors 5a and 5b.

An "injection syringe" is preferably understood as a syringe of small volume, that is to say a volume of between 1 ml and 3 ml. A "mixing syringe" is preferably understood as a syringe of large volume, that is to say a syringe with a volume greater than or equal to 10 ml.

Advantageously, the female connectors 5a and 5b are contiguous, which permits the connection of two contiguous mixing syringes.

Advantageously, the fluid circulation channel 10 brings only two of the connectors 5a, 5b, 5c and 6 of the stopcock 1 into communication. For this purpose, the fluid circulation channel 10 comprises only a single path provided with two openings 101 and 102 on the outer cylindrical wall 14. The use of the medical stopcock 1 is thus made safe. Indeed, only two paths are in communication regardless of the orientation of the plug 3, which makes it possible to perform three actions, but only one of these three actions at a time:

mixing a first substance and a second substance contained, respectively, in the mixing syringes 20 and 21, which are connected to the connectors 5a and 5b, or transferring some of the mixture obtained from the mixing of the first and second substances, and contained in one of the mixing syringes 20 and 21, into the injection syringe 22 connected to the connector 5c, or injecting into a patient, by way of a catheter connected to the connector 6, the mixture previously transferred into the injection syringe 22 connected to the connector 5c.

Thus, it will not be possible to inject the mixture or the emulsion into a patient while filling one of the mixing syringes or the injection syringe 22, or to mix the first and second substances contained in one of the mixing syringes, preferably the syringe 20, while transferring the emulsion or the mixture obtained into the injection syringe 22. The mixture is preferably an emulsion.

For this purpose, the fluid circulation channel 10 is L-shaped, which makes it possible to bring the mixing syringes 20 and 21 into fluidic communication, or to bring the mixing syringe 20 into fluidic communication with the injection syringe 22, or to bring the injection syringe 22 into fluidic communication with a downstream device such as a catheter 23 or a micro-catheter.

The plug 3 advantageously comprises visual indicators 18, such that the person using the stopcock 1 can tell, from the position of the plug 3, which connectors are in communication.

In the example shown, the indicators 18 are two arrows oriented at 90° to each other and showing the position of the fluid circulation channel 10.

Still more advantageously, as is shown in FIGS. 6 to 8, the plug 3, on the bottom of an upper part 30 carrying the lever 17 and the indicators 18, comprises a circular groove 31 that is interrupted by ribs 32 aligned with the visual indicators 18. On an upper part, the body 2 of the medical stopcock comprises a means preventing a rotation of the plug 3 that would establish a communication between the connector to which a mixing syringe is connected and the connector to which a downstream device is connected (that is to say would establish a communication between the connectors 5b and 6). This means is formed by a rib 202 which has a curved shape and which is designed to slide in the circular groove 31 between the ribs 32.

This stopcock thus permits the preparation of a mixture or an emulsion of two substances that are contained in mixing syringes 20 and 21 or permits filling of an injection syringe 22 from one of the mixing syringes (preferably the syringe 20) or permits injection of the obtained mixture or emulsion into a patient. The device according to the invention is thus preferably a three-way stopcock with four ports.

The position of the ribs 32 is preferably linked to the positon of the circular groove 31 on the plug 3. Thus, in another embodiment, the ribs could be positioned differently, that is to say they could be non-aligned with respect to the visual indicators, on condition that their positioning makes it possible to prevent communication between the conduits 2b and 2d.

Advantageously, the medical stopcock 1 comprises at least two gripping zones that are designed for the placement of a finger. These gripping zones allow the stopcock 1 to be grasped more efficiently, thereby making it easier to manipulate during the steps of connection or disconnection of the syringes 20, 21 and 22, or during the orientation of the plug 3 to permit communication between one or other connector.

In the example shown, the stopcock 1 comprises four gripping zones 15, which are formed by flat circular shapes projecting from the body 2. These gripping zones 15 are distributed between the connectors 5a, 5b, 5c and 6.

The medical stopcock 1 comprises a reinforcement collar 7 rigidly connected to at least two of the connectors of the medical stopcock 1. According to the invention, the reinforcement collar 7 is spaced apart from the central body 2 in order to form an openworked zone 9 around the central body 2. The fact that the reinforcement collar 7 is spaced apart from the central axis of the stopcock 1 makes it possible to distance the zone where stresses are concentrated and to reduce the effects of the stresses.

When a stress is applied to a plastic part, it generates a deformation. On the medical stopcock 1, this stress will be applied, for example, between two female Luer connectors 5b and 5c which are oriented at 90° with respect to each other during the mixing phase. The stress will thus deform the two connectors 5b and 5c by moving them toward each other. If it remains in what is called the range of "elastic deformation", the body of the stopcock 1 recovers its initial shape when this stress is terminated. If the elastic deformation range is exceeded, the material of the stopcock 1 then enters a phase of plastic deformation. When the stress is terminated, the stopcock 1 does not recover its initial shape. It thus retains a permanent deformation. In the mixing phases, there will additionally be a cyclical phenomenon of "plastic deformation", which will cause "fatigue" of the plastic material.

In the zones where stresses are concentrated, namely the sharp edges, the protruding zones, the drilled zones, the holes, some white zones will begin to form. These are the manifestation of a constriction zone. The material will lose some of its properties of mechanical strength, and this phenomenon will amplify until the material ruptures. The material will then crack and the stopcock will break.

If the stress applied is considerable, and if there is also an additional phenomenon of chemical attack by an oily solution, the stopcock 1 may become brittle directly, without going through the phase of plastic deformation. This is true of most of the standard perfusion stopcocks that are used in chemoembolization procedures (c-TACE).

The openworked zone 9 thus formed avoids the generation of shrink marks inside the body 2. The reinforcement collar 7 is therefore not in direct contact with the bore 200 in which the plug 3 is mounted rotatably.

Advantageously, the reinforcement collar 7 is rigidly connected to three or four connectors of the medical stopcock 1. In the example shown, the reinforcement collar 7 is rigidly connected to the four connectors 5a, 5b, 5c and 6 and forms a complete belt around the body 2, thereby improving the stability of the stopcock 1. The openworked zone 9, which in this embodiment will avoid any contact between the collar and the central barrel of the stopcock, makes it possible to avoid, to the maximum possible extent, the occurrence of shrink marks.

Strength tests carried out by way of example on the medical stopcock 1 have been able to confirm that, when the latter does not have a reinforcement collar 7, the elastic limit of the material is reached at a shearing force of 17 N, and that the zones where stresses are concentrated are located at the junctions between the connectors and the central body. In such a case, the risks of the stopcock 1 breaking are considerable.

By contrast, when the medical stopcock 1 is provided with the collar 7, the elastic limit of the material is reached at a shearing force of 35 N, and the zones where stresses are concentrated are located at the intersections of the collar 7 with the connectors. The risks of breaks and of shrink marks appearing are thus reduced.

According to an embodiment of the invention not shown here, the medical stopcock 1 can comprise just two female connectors and a male connector.

It is important that the intersection between the reinforcement collar 7 and each connector is remote from the thread 50 of the connector, or more generally from the functional zone of the connector, which is most often the distal end of this connector, since the functional zone is the connection port on which or in which is inserted, for example, a syringe or the locking ring of a hose or of a catheter.

The reinforcement collar 7 is made of the same material as the body 2. In this case, the medical stopcock 1 is formed in one piece and from the same material.

Alternatively, the reinforcement collar 7 is made of a material different than that of the body 2 and of the plug 3. In such a case, the medical stopcock 1 is formed in one piece but involves an operation of overmolding the collar 7, which has the advantage of strengthening the mechanical stability of the latter. The overmolding of the reinforcement collar 7 is carried out using "filled" plastic materials. A "filled plastic material" is understood as a material in which a solid, non-miscible substance called a "filler" has been dispersed at the moment of injection. Preferably, the filler is chosen from among the compounds of the following list: mineral fillers in the form of powders such as synthetic silica, organic fillers such as wood flour or fruit peel or cellulose paste, fibrous reinforcing fillers such as glass fibers, and non-fibrous reinforcing fillers such as hollow glass microspheres or synthetic silica. The fibrous reinforcing fillers are able to improve the mechanical characteristics, the thermal stability and the dimensional stability of the material. Preferably, the reinforcement collar 7 is overmolded on the body 2 using a material filled with fibers such as glass fibers.

The reinforcement collar 7 has a width L7 greater than its thickness e7, which thus makes it possible to improve the moment of inertia and hence the mechanical strength of the stopcock 1. The reinforcement collar 7 preferably has a width L7 which is 3 to 10 times, preferably 3 to 7 times, more preferably 3 to 5 times greater than its thickness e7.

Within the meaning of the present invention, an "openworked zone" is understood as a zone that is empty of material and shaped like a ring between the barrel of the body 2 of the stopcock 1 and the reinforcement collar 7. Preferably, as is shown in FIG. 2, said ring has an internal radius $r_a$, equal to the external radius $R_f$ of the barrel of the body 2, and an external radius $R_a$ equal to the internal radius $r_c$ of the reinforcement collar 7. The difference between $R_a$ and $r_a$ gives the width $l_a$ of the openworked zone 9. The width $l_a$ of the openworked zone 9 is preferably from 0.1 to 4 mm, more preferably from 1 to 2.5 mm, still more preferably from 1.5 to 2.5 mm.

Preferably, the reinforcement collar 7 is a ring of plastic material, or of another material as described below, forming the link between at least two Luer ports. The ring shape makes it possible to better dissipate the forces without generating a zone where stress is concentrated.

The internal radius $r_c$ of the ring is equal to the external radius $R_a$ of the openworked zone. The width $L_c$ of the ring is preferably from 1 to 20 mm, more preferably from 2 to 10 mm, still more preferably from 3 to 6 mm.

The thickness $e_c$ of this ring of plastic material, or of another material as described below, is preferably from 0.5 to 8 mm, more preferably from 1 to 5 mm, still more preferably from 1.5 to 2.5 mm.

The width $l_a$ of the openworked zone 9 between the reinforcement collar 7 and the barrel of the body 2 is preferably equal to the thickness e7 of the reinforcement collar 7.

This openworked zone 9 is produced, in the plastic injection molding equipment, by a mold insert. This mold insert, made of a steel alloy, is subject to very considerable forces (pressure) during phases of injection of the plastic material. These pressures can be from 500 to 2500 bar and more generally from 500 to 1500 bar. To these forces is added a temperature factor of the plastic material, injected into the cavity and coming into contact with the mold insert, from 150 to 300° C. This temperature causes substantial expansion stresses on this mold insert. The width $l_a$, still more preferably from 1.5 to 2.5 mm, makes it possible to preserve an optimal mechanical strength of the mold insert.

Preferably, the collar 7 must not have any surface in contact with the barrel of the body 2 of the stopcock 1.

Preferably, the gripping means 15 are situated on the reinforcement collar 7.

In the example shown, the projections 13a and 13b of the foolproofing device 13 extend from the reinforcement collar 7. In an alternative not shown, it is possible that the projections 13a and 13b are not connected to the reinforcement collar 7 and extend, for example, from the connector 5c or from the body 2.

According to an embodiment of the invention as shown in FIG. 9, it is possible for the medical stopcock 1 not to have gripping means, nor projections that form a foolproofing device and are provided on the reinforcement collar 7.

The body 2, the plug 3 and/or the reinforcement collar 7 forming the medical stopcock 1 are made from one or more materials that better withstand the mechanical and chemical stresses. Preferably, the body 2 and the reinforcement collar 7 are of a different material than the plug 3. The mechanical stresses are mainly the deformation by shearing and the pressure exerted on the stopcock 1 during its manufacture and/or its use. Moreover, the material from which the stopcock 1 is manufactured must be resistant to any pharmaceutical product, including oily products. Preferably, the material must be resistant to Lipiodol®. In addition or alternatively, the material of the body 2 and/or of the reinforcement collar 7 must be characterized by a high modulus of mechanical strength (Young's modulus). Thus, the medical stopcock 1, preferably its body 2 and its reinforcement collar 7, is made of the materials chosen from the following list: acrylonitrile butadiene styrene (ABS), copolymer of methyl methacrylate-acrylonitrile-butadiene styrene (MABS), polyester, polycarbonates (PC), alloys of polycarbonates, polysulfones, polyurethanes, polyether ketone ketone (PEKK), polyether ether ketone (PEEK), polyaryl ether ketones (PAEK), polymethyl methacrylate (PMMA), polyetherimides, polyamides (PA), preferably PA11 and PA12, polymethylpentene (TPX), polysulfone (PSU), cyclic olefin copolymers (COC), cyclic olefin polymers (COP), fluoroplastics other than polytetra-fluoroethylene (PTFE), phosphoenolpyruvate (PEP) and combinations of these materials (for example ABS-PC). Preferably, the medical stopcock 1, more preferably its body 2 and its reinforcement collar 7, is made of the materials chosen from the following list: acrylonitrile butadiene styrene (ABS), copolymer of methyl methacrylate-acrylonitrile-butadiene styrene (MABS), polycarbonates (PC), polyether ether ketone (PEEK), polymethyl methacrylate (PMMA), polyamides (PA), preferably PA11 and PA12, polymethylpentene (TPX), polysulfone (PSU), cyclic olefin copolymers (COC), cyclic olefin polymers (COP). Still more preferably, the medical stopcock 1, more preferably its body 2 and its reinforcement collar 7, is made of the materials chosen from the following list: polyether ether ketone (PEEK), polymethyl methacrylate (PMMA), polyamides (PA), preferably PA11 and PA12, polymethylpentene (TPX) and polysulfone (PSU). Preferably, the medical stopcock 1 comprises polyamide or is composed of polyamide.

Preferably, the plug 3 of the stopcock is made of a softer material than the body 2 and/or than the reinforcement collar 7 of this stopcock. Thus, the plug 3 of the stopcock is preferably made of the materials chosen from the following list: polyethylene (PE), polypropylene (PP), polyoxymethylene (POM) or polybutylene terephthalate (PBT). This material must allow the plug 3 to be able to conform slightly within the body 2 of the stopcock. Moreover, the fact that the body 2 and the plug 3 are made of different materials makes it possible to improve the properties of rotation of the plug 3 in the body 2 of the stopcock. The plug 3 is more preferably made of POM.

Advantageously, the female connectors 5a, 5b and 5c are inlet ports, while the male connector 6 is an outlet port.

In one embodiment, the male connector 6 comprises a locking ring 8, which is fixed. This ring is therefore rigidly connected to the connector 6 and, more generally, to the body 2 of the stopcock 1.

Preferably, and in the example shown, the male connector 6 comprises a locking ring 8 which is clipped onto the distal end of the male connector 6. The locking ring 8 is movable and makes it possible to strengthen the connection of the male connector 6 to a female connector of a downstream device (for example a catheter or a microcatheter). More preferably, the locking ring 8 turns on the axis of the male connector 6, which for its part remains fixed. This has the advantage of making the connection manipulation easier while at the same time reducing the risk of disconnection.

As is shown in FIG. 12, the medical stopcock 1 permits formation of a preparation kit K for preparing a product to be injected, preferably a mixture or an emulsion, with two mixing syringes 20 and 21 and an injection syringe 22. The female connectors 5a and 5b are connected to a first mixing syringe 20 and to a second mixing syringe 21, respectively, and the female connector 5c comprising the foolproofing device 13 is connected to an injection syringe 22.

The preparation kit can also comprise a downstream device, such as a catheter 23 or a microcatheter permitting the injection, into a patient, of the product to be injected that is contained in the injection syringe 22. The catheter 23 is mounted and locked on the male connector 6 by virtue of the locking ring 8.

Preferably, it is the connector arranged on the path of communication with a downstream device, such as a catheter 23 or a microcatheter, that comprises a foolproofing device 13. Preferably, the foolproofing device according to the present invention prevents the connection of at least one of the elements of the kit, still more preferably of at least two of the elements of the kit. Still more preferably, the foolproofing device according to the present invention prevents the connection of the mixing syringes 20, 21.

Preferably, the kit elements whose connection is prevented by the foolproofing device are provided with means prohibiting their connection to the connector that comprises the foolproofing device. These means prohibiting the connection of elements of the kit to the connector that comprises the foolproofing device are preferably fins situated at the end of said elements of the kit.

The preparation kit can also comprise accessories for collecting the solutions, facilitating the filling of the mixing syringes 20 and 21.

The preparation kit K permits the implementation of a method for preparing a mixture or an emulsion intended to be injected into a patient. This method comprises the following steps. In a first step, two mixing syringes 20 and 21 are mounted on two corresponding female connectors 5a and 5b.

In a second step, which can be carried out at the same time as the first step, the injection syringe 22 is mounted on the female connector 5c comprising the foolproofing device 13.

Preferably, the mixing syringes 20 and 21 respectively contain an aqueous solution and an oil, preferably an iodinated oil. Said aqueous solution comprises at least one anticancer agent and, optionally, at least one densifying agent.

Advantageously, the anticancer agent that the aqueous solution present in one of the two mixing syringes can comprise is chosen from among the anthracyclines and, more preferably, from among doxorubicin, epirubicin, nemorubicin and idarubicin. In an advantageous embodiment, the aqueous solution can thus additionally comprise a densifying agent, preferably at least one non-ionic iodinated contrast medium. The non-ionic iodinated medium, which can be used as such as a densifying agent, is preferably chosen from among iobitridol (Xenetix®), iopamidol (Iopamiron®, Isovue®), iomeprol (Iomeron®), ioversol (Optiray®, Optiject®), iohexol (Omnipaque®), iopentol (Imagopaque®), ioxitol (Oxilan®), iopromide (Ultravist®), metrizamide (Amipaque®), iosarcol (Melitrast®), iotrolan (Isovist®), iodixanol (Visipaque®), iosimenol and iosimide (Univist®), and a mixture of these. Iobitridol is the preferred non-ionic iodinated medium.

Advantageously, the iodinated oil that one of the mixing syringes can contain comprises or is composed of iodinated fatty acid derivatives, preferably iodinated fatty acid ethyl esters, more preferably iodinated fatty acid ethyl esters of poppy seed oil, of olive oil, of rapeseed oil, of peanut oil, of soybean oil or of walnut oil, still more preferably iodinated fatty acid ethyl esters of poppy seed oil or of olive oil. More preferably, this iodinated oil comprises or is composed of iodinated fatty acid ethyl esters of poppy seed oil, also called blue seeded opium poppy or *Papaver somniferum* var. *nigrum*.

A third step consists in mixing the aqueous solution contained in the mixing syringe 20 with the oil contained in the mixing syringe 21, after positioning the plug 3 in such a way as to bring the mixing syringes 20 and 21 into communication by way of the conduits 2a and 2b, and effecting a reciprocating motion of the pistons of the mixing syringes 20 and 21 until a mixture or an emulsion is obtained.

Thereafter, in a fourth step, some or all of the mixture or of the emulsion obtained in the mixing step is transferred into the injection syringe 22, after positioning the plug 3 in such a way that the mixing syringe 20, into which some or all of the mixture or of the emulsion obtained in the mixing step has been transferred, is brought into communication with the injection syringe 22 by way of the conduit 2a and the conduit 2c.

Preferably, the fourth step is carried out once the user of the stopcock determines visually that the mixture or the emulsion is homogeneous.

The catheter 23 is fitted simultaneously with the mixing syringes 20 and 21 and/or with the injection syringe 22, or after the mixing step has been carried out, or after the step of transferring some of the mixture or of the emulsion into the injection syringe 22. Preferably, the catheter 23 is mounted on the male connector 6 after this fourth transfer step has been carried out.

By positioning the plug 3 in such a way that the injection syringe 22 is in communication with the catheter 23, and by then actuating the piston of the injection syringe 22, the mixture or the emulsion can then be injected directly into a patient.

Once the mixing syringes 20 and 21, the injection syringe and the catheter 23 have been connected to the stopcock 1, an additional step of mixing the mixture or the emulsion obtained in the third step can be performed, in the case where the user determines visually that the mixture or the emulsion has undergone phase separation. This is an important advantage of the stopcock according to the invention over the other stopcocks of the prior art, which require disconnection of the mixing syringes or of the injection syringe, thus increasing the risks of air entering the injection device.

The mixing syringe 20 is brought into communication with the injection syringe 22, or the injection syringe 22 is brought into communication with the catheter 23, by suitably positioning the fluid circulation channel 10 of the plug 3 by a rotation movement of the lever 17. The correct positioning of the plug 3 for the preparation step to be carried out is verified with the aid of the arrow-shaped indicators 18. By way of example, in FIG. 12, the plug 3 is positioned in such a way as to bring the connectors 5a and 5b into fluidic communication, as indicated by the arrows 18, in order to permit mixing of the contents of the mixing syringes 20 and 21.

The foolproofing device 13 eliminates the risk of a mixing syringe 20 or 21 being connected to the connector 5c intended for the injection syringe 22 and prevents errors from being committed in the preparation of the mixture that is to be injected into the patient. By virtue of the foolproofing device 13, there is only one female connector on which the injection syringe 22 can be mounted, and the mixing syringes 20 and 21 can only be mounted on the remaining female connectors, which are positioned in a contiguous manner. This ensures the reliability of the medical stopcock 1.

In the case where the medical stopcock 1 comprises only two female connectors and a male connector, the injection syringe 22 is mounted on one of the female connectors in place of one of the mixing syringes 20 and 21, once the mixture or the emulsion has been prepared and has been transferred into one of the mixing syringes 20 and 21.

The features of the embodiments and variants described above can be combined to form new embodiments of the invention.

The invention claimed is:

1. A medical stopcock comprising:
 a body provided with at least two female connectors and a male connector;
 a mobile plug, which is mounted in the body, is provided with a rotation lever and comprises a fluid circulation channel; and
 a reinforcement collar rigidly connected to at least two of the connectors;
wherein the reinforcement collar is spaced apart from the body in order to form an openworked zone around the body.

2. The medical stopcock as claimed in claim 1, wherein said stopcock comprises four connectors, of which three are female connectors, and wherein the reinforcement collar is rigidly connected to three or four connectors.

3. The medical stopcock as claimed in claim 1, wherein said stopcock comprises at least two gripping means designed for the placement of a finger, and situated on the reinforcement collar.

4. The medical stopcock as claimed in claim 1, wherein the reinforcement collar is made of the same material as the body.

5. The medical stopcock as claimed in claim 1, wherein the reinforcement collar is made of a material different than that of the body and that of the mobile plug.

6. The medical stopcock as claimed in claim 5, wherein the reinforcement collar is made of a fiber-reinforced material and is overmolded on the body.

7. The medical stopcock as claimed in claim 1, wherein the mobile plug is made of a material that is softer than the body and/or than the reinforcement collar.

8. The medical stopcock as claimed in claim 1, wherein the reinforcement collar has a width greater than its thickness.

9. The medical stopcock as claimed in claim 1, wherein at least one of the female connectors is designed to receive an injection syringe and comprises a fool proofing device in order to prevent a mixing syringe from being mounted on this connector, and wherein this fool proofing device is formed by two projections which extend from the reinforcement collar and are provided on each side of the female connector designed to receive an injection syringe and form insertion spaces with respect to this connector.

10. The medical stopcock as claimed in claim 9, wherein the projections make it possible to prevent the mounting of syringes that are provided with a means prohibiting their connection to the female connector designed to receive an injection syringe.

11. A preparation kit for preparing a product to be injected, wherein said preparation kit comprises:
   a medical stopcock as claimed in claim 1;
   two mixing syringes designed to be connected to a first and a second female connector of the stopcock; and
   an injection syringe designed to collect at least some of the product obtained by the mixing of the contents of the mixing syringes, effected by a reciprocating motion of the pistons of said mixing syringes, and designed to be connected to one of the female connectors of the stopcock.

12. The preparation kit as claimed in claim 11, wherein one of the female connectors of the stopcock comprises a fool proofing device, and wherein the mixing syringes comprise a means prohibiting their connection to said female connector.

13. The preparation kit as claimed in claim 12, wherein the mixing syringes comprise fins at their end.

14. A method for preparing a mixture or an emulsion intended for injection into a patient, wherein the method comprises steps of:
   a) connecting two mixing syringes to two corresponding female connectors of a medical stopcock as claimed in claim 1;
   b) mixing an aqueous solution, contained in one of the mixing syringes, with an oil contained in the other mixing syringe after positioning a mobile plug of the medical stopcock in such a way as to bring the mixing syringes into fluidic communication with each other, and effecting a reciprocating motion of the pistons of these mixing syringes until a mixture or an emulsion is obtained;
   c) connecting an injection syringe to a specific connector of the medical stopcock or in place of the mixing syringes; and
   d) transferring some or all of the mixture or emulsion obtained in step b) into the injection syringe after positioning the mobile plug in such a way as to bring one of the mixing syringes into communication with the injection syringe.

15. The preparation method as claimed in claim 14, wherein the method additionally comprises a supplementary step of connecting a downstream device to a male connector of the medical stopcock, this supplementary step being either concomitant with step a), or subsequent to step b), or concomitant with step c), or subsequent to step d).

* * * * *